United States Patent
Seliger et al.

(10) Patent No.: US 6,993,556 B1
(45) Date of Patent: Jan. 31, 2006

(54) CONTEXT ADMINISTRATOR

(75) Inventors: Robert Seliger, Winchester, MA (US); Elaine Seliger, Winchester, MA (US); David Fusari, Groton, MA (US)

(73) Assignee: Sentillion, Inc., Andover, MA (US)

(*) Notice: Subject to any disclaimer, the term of this patent is extended or adjusted under 35 U.S.C. 154(b) by 0 days.

(21) Appl. No.: 09/545,396

(22) Filed: Apr. 7, 2000

Related U.S. Application Data

(60) Provisional application No. 60/128,145, filed on Apr. 7, 1999, provisional application No. 60/135,907, filed on May 25, 1999, provisional application No. 60/136,670, filed on May 28, 1999, provisional application No. 60/139,235, filed on Jun. 14, 1999, provisional application No. 60/139,145, filed on Jun. 14, 1999, provisional application No. 60/146,722, filed on Aug. 2, 1999, provisional application No. 60/145,681, filed on Jul. 26, 1999.

(51) Int. Cl.
*G06F 15/16* (2006.01)

(52) U.S. Cl. ............ 709/203; 709/217; 709/219; 718/107; 718/108; 705/3; 705/4

(58) Field of Classification Search ........ 709/202–203, 709/217, 219, 229; 718/107–108; 705/2, 705/3–4
See application file for complete search history.

(56) References Cited

U.S. PATENT DOCUMENTS

| | | | | |
|---|---|---|---|---|
| 5,491,817 A | * | 2/1996 | Gopal et al. | 707/200 |
| 5,805,786 A | | 9/1998 | Badovinatz et al. | 395/182.02 |
| 6,064,973 A | * | 5/2000 | Smith et al. | 705/7 |
| 6,119,145 A | * | 9/2000 | Ikeda et al. | 709/203 |
| 6,134,594 A | * | 10/2000 | Helland et al. | 709/229 |
| 6,205,476 B1 | * | 3/2001 | Hayes, Jr. | 709/220 |
| 6,237,092 B1 | * | 5/2001 | Hayes, Jr. | 713/100 |
| 6,260,021 B1 | * | 7/2001 | Wong et al. | 705/2 |
| 6,377,994 B1 | * | 4/2002 | Ault et al. | 709/229 |
| 6,401,138 B1 | * | 6/2002 | Judge et al. | 719/328 |
| 6,510,466 B1 | * | 1/2003 | Cox et al. | 709/229 |

FOREIGN PATENT DOCUMENTS

EP  0 803 808 A  10/1997

OTHER PUBLICATIONS

Context Management ("CCOW") Specification Subject Data Definitions, Version CM-1.1, Nov. 6, 1999, pps. 1-28.
Context Management ("CCOW") Specification User Interface: Microsoft Windows, Version CM-1.1, Nov. 6, 1999, pps. 1-18.
Context Management CCOW Specification Component Technology Mapping: Active X, Version CM-1.1, Nov. 6, 1999, pps. 1-48.
Context Management (CCOW) Specification Technology- and Subject -Independent Component, Architecture Version CM-1.1, Nov. 6, 1999, pps. 1-228.
David Adams, "Solstice- Access System Administration Tools With a Graphical User Interface", XP002154495, (1995).

(Continued)

*Primary Examiner*—Ario Etienne
*Assistant Examiner*—LaShonda Jacobs
(74) *Attorney, Agent, or Firm*—Wolf, Greenfield & Sacks, P.C.

(57) ABSTRACT

A context management and administration system includes a context manager, which manages the context of plural applications programs, and an administration suite, which oversees and manages the manager. Context administration can include setting up and maintaining subject data definitions, intervening in context manager operations, providing security functions to protect sensitive context information against tampering by unauthorized users, etc.

32 Claims, 1 Drawing Sheet

OTHER PUBLICATIONS

David Adams, "Lpstat-Print Information about the Status of the Print Service", XP002154496 (1995).

David Adams, "Cancel-Cancel Print Request", XP002154497 (1995).

David Adams, "Lpshut-Stop the LP Print Service", XP002154498 (1995).

David Adams, "Ifconfig-Configure Network Interface Parameters", XP002154499 (1995).

Grubb et al., "Single Sign-On and the System Administrator", XP002154500 (1998).

David Adams, "Intro, Intro-Introduction to Maintenance Commands and Application Programs", XP002154501 (1995).

Clinical Context Working Group: "The Clinical Context Object Workgroup: Its Standard and Methods", XP002154044, (1998).

* cited by examiner

CONTEXT ADMINISTRATOR

CROSS-REFERENCE TO RELATED APPLICATIONS

This application claims domestic priority under 35 U.S.C. § 119(e) to provisional U.S. patent application Ser. No. 60/128,145 filed Apr. 7, 1999, Ser. No. 60/135,907 filed May 25, 1999, Ser. No. 60/136,670 filed May 28, 1999, Ser. No. 60/139,235 filed Jun. 14, 1999, Ser. No. 60/139,145 filed Jun. 14, 1999, Ser. No. 60/146,722 filed Aug. 2, 1999, and Ser. No. 60/145,681 filed Jul. 26, 1999, all now abandoned, and incorporated herein in their entirety by reference.

FIELD OF THE INVENTION

The present invention relates to tools for managing and administering the management of context in software applications.

BACKGROUND OF THE INVENTION

There are many businesses or fields of endeavor, which rely on the use of plural desktop computer applications. One such field is the modern practice of medicine. In such a setting, users quite often find themselves entering and reentering similar information over and over. For example, a single user may have to repeat login information in plural applications, followed by the same or similar client information. Such information, that defines the environment in which each application operates is known as context. That is, context is a collection of data items and corresponding values, wherein the items represent information required in common between plural applications in an industry or business setting. For example, in health care, a patient identifier (patient ID) is an item which is part of the context in which plural clinical applications may participate, or share.

In the modern practice of medicine, a physician or other professional or staff member may need to store, retrieve, analyze, etc. various types of patient data. The patient data to be processed may be clinical; e.g. x-ray images or blood work results, or may be financial, e.g. insurance cover and billing history. Thus, clinical applications, such as those to store, retrieve and display x-ray images and those to store, retrieve and display blood work results have inputs and outputs which fall into two broad classes: highly specialized, work product specific I/O; and more general, context-related I/O.

The desirability of managing context information, so that a user at a workstation need not reenter information such as user identification (user ID) or patient identification (patient ID) has long been recognized.

A standard known as Health Level Seven Context Management Specification Version CM-1.1 was promulgated by the Health Level Seven (HL7) Clinical Context Object Workgroup (CCOW) on Nov. 6, 1999, incorporated herein in its entirety by reference, to define an interface and other architectural definitions of a Context Management Architecture (CMA), whereby clinical applications interact with a Context Manager to manage context information across a range of clinical and other health care related applications.

At this time, there are no other known, comprehensive context management software packages available. Some small steps have been taken for example to share context amongst one publisher's own titles, using proprietary methods absent a context manager, or to permit a user to sign onto a single application which transfers user context to plural other applications. However, no context manager handling both user and patient context is known, much less a complete system with central administration of the context management process.

SUMMARY OF THE INVENTION

What is desired is a context administrator and method which solves the problems associated with settings using plural, unrelated software applications to process data related to a common context.

As discussed above, context is a collection of data items and corresponding values, wherein the items represent information required in common between plural applications in an industry or business setting. For example, in health care, a patient identifier (patient ID) is an item which is part of the context in which plural clinical applications may participate, or share. The data items comprising context are organized into subjects. For example, subjects defined by HL7 CCOW CM-1.1 include User, Patient and Encounter. In accordance with some aspects of the invention, a subject definition is a data structure including the following parts:

Name (The Name must be correctly formatted per the CM-1.1 standard because attempting set the context data for an unknown subject is invalid and enforced by the context manager, as specified by the CM-1.1 standard.)

IsSecure (If true, IsSecure indicates that only applications specifically configured to be participants to that subject can get the subjects context data. Additionally, some applications can be identified as "trusted," meaning that they can change the subject's context data, as specified by the CM-1.1 standard.)

List of Applications (The List of Applications identifies those configured for the subject and which ones are "trusted".)

List of Correctly Formatted Item Names for the Subject (This List gives the names of the fields that the subject is allowed to contain. Each name must be correctly formatted per the CM-1.1 standard. Each item name may be one defined in the standard or it may be formatted as a custom item name, where the format is per the CM-1.1 standard.)

List of Dependent Subjects (One subject may be dependent on another, meaning that if the dependent subject's context is changed, this subject's context data is cleared, as specified in the CM-1.1 standard.)

On the subject of Dependent Subjects, the CM-1.1 standard has the following remarks:

For simplicity, it is generally desirable that there not be any semantic dependencies between context subjects. This enables an application to set a context subject without concern for the other available subjects.

With this assumption, it is possible for an application to independently set the context data items for just one subject, some, or all subjects during the course of a single context change transaction. A context subject whose items have not been set by the application shall remain as it was prior to the transaction.

However, in certain cases it is necessary to define and enforce semantic inter-dependencies between context subjects. The only inter-dependencies that shall be defined and enforced are those that stipulate that a specific set of additional subjects that must be set each time a particular subject is set.

For example, whenever subject X is set by an application, the application must also set subject Y. These dependencies shall be enforced by the context manager. This notion of subject inter-dependency also necessitates an additional assertion, which is that if setting X requires that Y also be set, then whenever Y is set and X is not set, the value for X shall not be post-filled by the context manager. Instead, it shall appear after the context change transaction as though X is empty.

The inter-dependencies for standard subjects are documented in the document Health Level-Seven Standard Context Management Specification, Subject Data Definitions. [Ed. Note: the referenced document is part of the CM-1.1 standard.]

Inter-dependencies for custom subjects may be stipulated by the organization that defines the custom subject. A custom subject may be dependent upon any other subject. However, a custom subject may not require that a standard subject, or a custom subject defined by another organization, be dependent upon it. In other words, custom subject X can not assert that it must always be set whenever standard subject Y is set.

As used herein, context management is a process of storing, retrieving, modifying and communicating context information between a user and one or more applications, or between the plural applications used in a particular setting. For example, in health care, when a doctor switches from a heart monitor application to a blood analysis application, the patient ID need not be reentered if context management has been implemented. As used herein, context administration is a process of storing, retrieving, modifying and communicating information by which a context management system is controlled or supervised. A single context administrator may supervise multiple context managers or may supervise only one context manager.

According to one aspect of the invention, there is a method of administering a context management system, comprising configuring a subject data definition. The method may further include identifying one or more available context managers to administer. Identifying may also further include pinging possible context manager addresses to find the available context managers.

One type of data useful for security purposes is a shared secret. Thus, according to this aspect of the invention, the method may include maintaining in a subject data definition, a list or other means of identifying applications that are allowed to transact on that subject. The method may further include storing with each application a value, which is a function of, but not equal to a passcode for the application, so that the identity of an application desiring to transact on a secure subject can be verified. The method may yet further include encrypting the passcode to form the value. Methods embodying the invention can further include maintaining an inventory of applications whose context is managed; and maintaining a map relating users to user identifiers formatted for each application in the inventory. When the steps of maintaining are included, the method can also include identifying for each context, which applications share the context. In yet another variation, the method can configure communication parameters for the available context managers, generate a status report for the system or intervene in a context management process. Interventions can include forcing an application out of a context, canceling a transaction in progress or shutting down a context manager. Methods embodying aspects of the invention can include communicating with a context manager using a hypertext transport protocol. In some embodiments, the hypertext transport protocol is HTTP 1.1.

According to other aspects of the invention, embodiments thereof can include a context management and administrative system, comprising a context manager; and an administration suite. The administration suite can further include a context administrator; and a context server. The context server can further include a passcode service; a user-mapping agent (UMA) service; and a lightweight directory access protocol (LDAP) service. The LDAP service can further provide a data storage module in which the passcode service stores encrypted passcodes and in which the user-mapping agent service stores user mapping data. The context server can further include a registry in which the context manager is registered. Finally, the context server can further include configuration memory holding a common configuration used as a default configuration for the context manager.

BRIEF DESCRIPTION OF THE DRAWINGS

In the drawings, in which like reference designations indicate like elements.

DETAILED DESCRIPTION

The invention will be better understood upon reading the following description of an embodiment of our invention in connection with the drawings. This embodiment is described in connection with the administration of a software system, software components and software architecture for performing context management to synchronize a plurality of application programs to a single context. A block diagram of the embodiment is given in FIG. 1. The illustrated embodiment complies with the HL7 CCOW CM-1.1 standard. Thus, this embodiment can perform context management in a health care environment including CM-1.1 compliant clinical applications. Other standards for context management protocols and interfaces may exist, particularly outside of health care, for which the present invention is applicable. Regardless of the existence of such standards, while the present invention is described in connection with an application of the principles thereof to the health care industry, the invention may be practiced in connection with any industry that relies on plural applications for which context can preferably be managed or synchronized.

Figure 1:
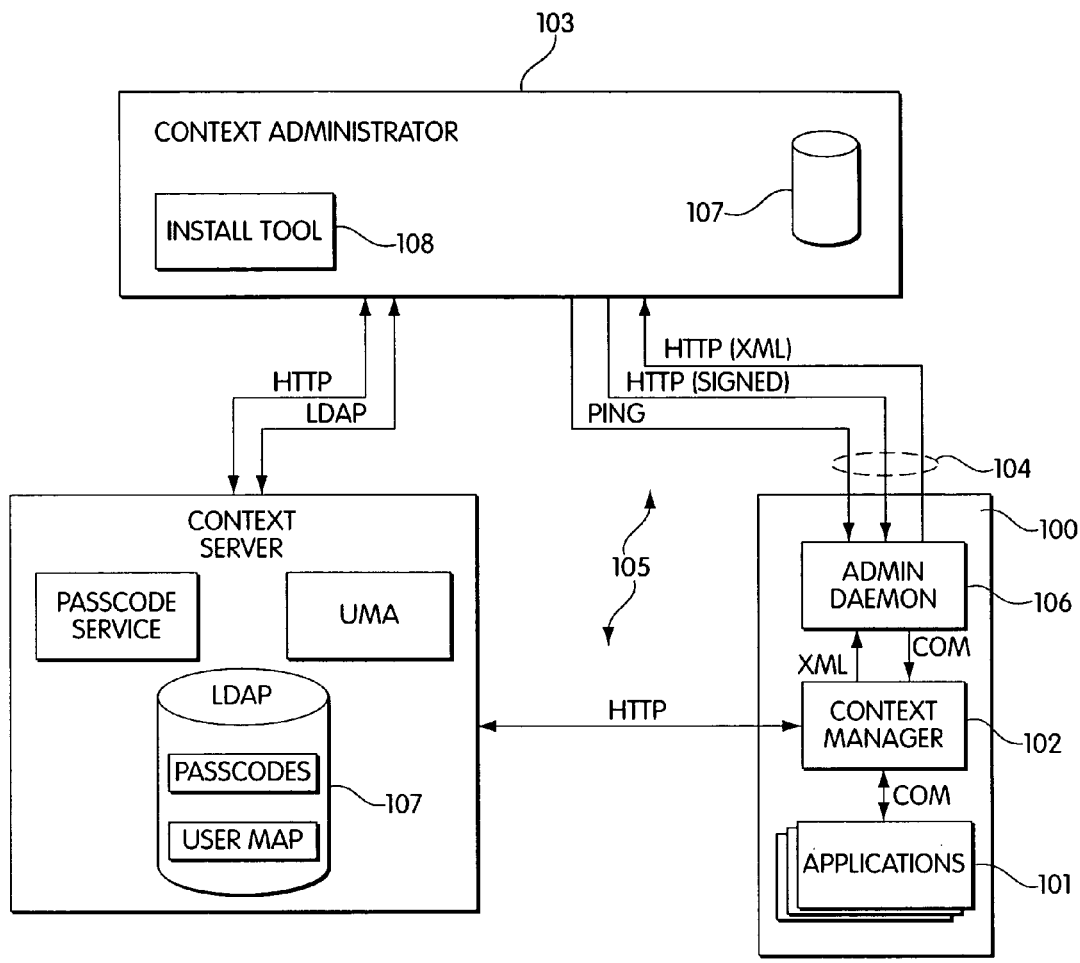
FIG. 1 is a schematic block diagram of a system embodying aspects of the invention.

The overall architecture of FIG. 1 is now briefly described.

One or more computer systems, workstations, desktop personal computers (PCs) or the like 100 have executing thereon one or more applications 101, e.g., in the health care field, clinical applications. It is assumed that context management of the applications 101 is desired, and that they comply with at least one standard for context management protocols and interfaces, e.g., HL7 CCOW CM-1.1. A context manager 102, also executing on a computer system, workstation, desktop PC or the like communicates with the applications 101 through an interface and using a protocol defined by standard. The context manager may or may not be executing on the same computer system, workstation, desktop PC or the like as the applications, but may communicate with the applications through a communications network. In the case of an HL7 CCOW CM-1.1 compliant system, Microsoft®COM protocol defines one layer of the communication protocol.

Administration functions may be remote from the managed computer systems, workstations, desktop PCs, etc., for example as an independent software module or program resident on a context administration console 103. The console 103 communicates with the system 100 on which the applications 101 reside through a channel 104 which may pass through an interconnection network, e.g., the Internet, an intranet, a Local Area Network (LAN), a Wide Area Network (WAN) or the like 105. In order to simplify communication through the interconnection network 105, a standard printable-character based protocol, such as the Hypertext Transport Protocol (HTTP) may be used. Messages transported by HTTP may be formatted as headers, Hypertext Markup Language (HTML) files, Extended Markup Language (XML) files, etc. Other protocols and message formats may alternatively be used. A daemon 106, resident on each of the systems 100, translates the protocol used for communication over the interconnection network (e.g., HTTP) into that used for context management of the applications (e.g., COM). The daemon 106 may alternatively be part of the context manager 102.

A database 107 of context information is maintained either on the context administration console or separately. When a context management installation tool 108 is invoked, similar links are established using an administration daemon 109 to draw current, common context information from the database 107, to set up the context of newly installed applications 100. This administration function can be performed at other times, as well, such as when a stand-alone system is brought into the context managed environment.

Although both the foregoing and the following discussion is given with respect to HL7 CCOW CM-1.1, HTTP 1.1, COM and health care clinical settings in particular, it will be apparent from the discussion that the inventors contemplate adaptations of the concepts illustrated to other industries and settings, some suggestions for which have been given.

For convenience, and without loss of generality, modules, programs and machines, particularly machines executing software programs are referred to herein as modules. In this document, modules could be function or procedure calls in a software program, a program module, a complete program, a machine executing a program or any part of a program, and the like, where a module performs a defined portion of the overall function of the system described.

It should be noted that the architecture described above appears to assume a particular partitioning of the context management and context administration task into individual modules, as evidenced by the blocks of FIG. 1. That apparent assumption, of course, is that there is a context manager module, a context administrator module and a context server module. However, the inventors have found that the context manager and context server can be combined in a single module in which the functions are shared in such a way as to behave as a single functional block. Alternatively, the context administrator and context server can be combined in a single module in which the functions are shared in such a way as to behave as a single functional block. Finally, all three separately described functional elements can be combined in a single module in which the functions are shared in such a way as to behave as a single functional block. These variations have important implications for the design of the communications and user interface portions of the system because communication between more tightly coupled functional elements, such as within a module, is easier and more secure than between more loosely coupled elements, such as between modules, and because the user interface can ultimately be defined using standard elements of a page markup language interpreted by a browser, rather than a proprietary ad hoc interface design.

Figure 2:
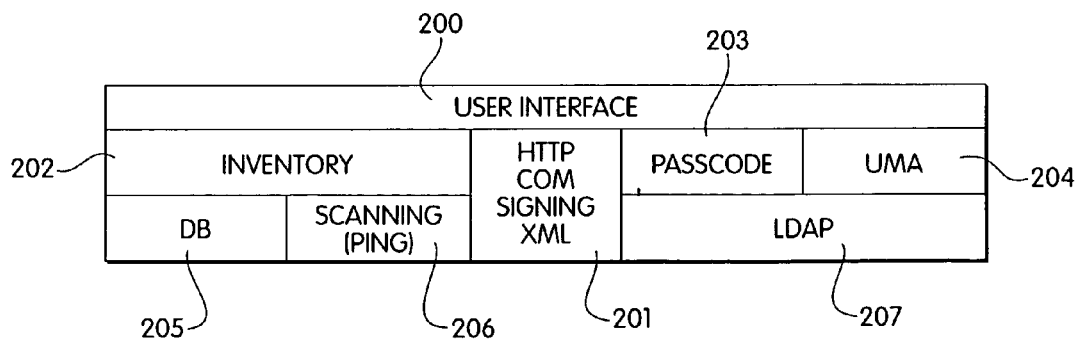
FIG. 2 is an organizational map of one software embodiment of aspects of the invention.

A context management and administration system according to a presently preferred embodiment of the invention has been implemented using the Microsoft Java programming language. The structure of the code is illustrated in FIG. 2.

A top layer, over all, is the user interface 200. This may be implemented using a conventional presentation manager available as a resource in many operating systems, or using a markup language such as HTML or the like and HTTP so that it can use a standard browser as the display module. Beneath the user interface layer, and tunneling through both lower layers is the HTTP, COM, signing and XML communication facility 201 used by all layers. An inventory facility 202, passcode facility 203 and user mapping agent facility 204, all described below, exist in the second layer. Finally, the third layer embodies the low-level functions of database management 205, scanning the network (pinging) 206 and Lightweight Directory Access Protocol (LDAP) 207, also all described below.

The following description explains the operation of the components of the architecture described above.

The context administrator, which is connected to a communication network through which it can communicate with other elements of the system, compiles an inventory of context managers available to it on the network. The context administrator determines whether a context manager is available at each legal network address by pinging at each address a communication port registered with the Internet Assigned Numbers Authority (IANA). When a context manager is configured to respond to messages on the registered port, at the address pinged, it responds. The context administrator can then build a database of available context managers. The database can be presented to users in a tree form, similar to the tree used in the Windows™ Explorer program used to navigate through files and folders on a computer hard disk.

The inventory can alternatively be built and updated automatically as context managers join or leave a network. In order to do so, each context manager will register itself to the context administrator by transmitting an identifier, for example a DCE UUID, "hello" message to the context administrator. The identifier needs to be unique within a given network.

As part of inventory management, a context manager can be removed from inventory, making it invisible to the context administrator. A context manager manually removed by a user of the context administrator then continues to function normally, but cannot be configured, etc. by the context administrator.

Once an inventory of context managers exists, the context administrator can then configure the context managers, obtain status from the context managers, perform interventions on the context managers and produce human- or machine-readable outputs communicating various types of information about the context administration process. It is also possible to view a human-readable listing of all operations performed by the context administrator. The listing is updated or appended to each time an operation is performed.

Configuring the context managers is a wide-ranging task, defining how a particular instance of a context manager behaves, as well as defining site-wide information relevant to the operation of all context managers under administration. Examples of configuration parameters defining how a particular instance of a context manager behaves include the parameters related to the details of performing a transaction, such as timing parameters. Examples of configuration parameters which affect an entire site include defining which applications will join in a particular context, passcodes and other security settings, and the subjects defined by the standard, including User, Patient and Encounter, required by the standard, and optional customizable subjects.

Configuring the security settings includes defining values in a database identifying which subjects are available only through a secure connection. For example, User is a secure subject. Defining a subject as secure necessitates that trusted participants be identified, as they can only access the subject, for example for viewing or editing, provided they give the passcode identifying them as a trusted participant. In the preferred embodiment, a trusted participant is one which will be allowed to edit the contents of a secure subject. In the HL7 CCOW CM-1.1 standard, User is a secure subject.

The contents of a subject are now illustrated by describing the subject, User. The subject User is used to configure who the users are within a particular site, for example. A user mapping agent identifies each user by a unique, site-wide User Identification (User ID). The User ID is linked to the individual login identifiers, such as username and password, used to obtain access to each individual application. This map of User ID to login identifier is housed on the context server module described above.

Status information which can be obtained by the context administrator can include one or more of the version number of each context manager in the inventory, which context managers have joined a particular context, what changes have been processed by each context manager, what changes have been aborted by each context manager, etc. Status information can also include a complete record of the current configuration of each context manager, so that if a context manager inadvertently becomes out of sync with the changes made by the context administrator, as determined by making a status inquiry, that context manager can be brought back into sync. Finally, status can also include a log of exceptions which may occur from time to time during operation. The log may contain the date and time of each event, the severity of the event and a message describing the event.

In some circumstances, intervention in the operation of individual context managers may be required. The context administrator module can be configured to force an application to leave a context, cancel a transaction in progress, remotely shut down an aberrantly behaving context manager or remotely restart a context manager.

According to a preferred embodiment, all outputs of the context administrator can be printed, sorted, exported to XML, etc., so as to be available in both human- and machine-readable form.

Context changes are effected in the system by means of transactions. In the health care field, HL7 CCOW CM-1.1 defines what constitutes a transaction. According to this standard, a secure transaction occurs as follows:

This method is similar to ContextData::SetItemValues. [See CM-1.1.] The primary difference is that the context participant's digital signature shall be provided as the value of the input appSignature when secure subject item values are among the items to be set. This signature enables the context manager to authenticate that they came from a designated application or from a valid secure subject mapping agent, and that the values were not tampered with between the time they were sent and were received.

A signature is not required when the values for the user subject items are null. This enables any application to set the user context to empty. When a signature is not provided, the value of the input appSignature shall be an empty string (" ").

Concatenating the string representations of the following inputs in the order listed shall form the data from which a message digest is computed by the participant:
 participantCoupon
 itemNames (i.e., All the elements in the order that they appear in the array.)
 item Values (i.e., All the elements in the order that they appear in the array.)
 contextCoupon A participant shall compute its digital signature by encrypting the message digest with its private key.

The exception SignatureRequired is raised if the value of appSignature is not a digital signature and a signature is required in order to perform this method.

The exception AuthenticationFailed is raised if a digital signature is required and provided, but the process of authentication determines that: the application that invoked this method did not previously provide its public key via the interface SecureBinding; that the input appSignature has been forged; that the input parameter values have been tampered with; that the participant has not been designated for performing user context changes.

We now return to FIG. 1, to discuss how the illustrated architecture provides the facility for performing the operations described.

The context administrator module contains the logic defining the overall operation of the system. The actual maintenance and switching of context is performed by the context manager module. A variety of support functions are provided by the context server. For example, the context server may include a passcode service, a user mapping agent service and a LDAP service. These services are now discussed.

The passcode service provides a virtual software vault for the passcodes. Passcodes are stored in encrypted form in the LDAP data store accessed by the context server. Passcodes are not themselves ever transmitted as messages, but rather the context manager sends a signed HTTP message to the context server, which checks the signature and contents of the message against the stored, encrypted passcode. An MAC acknowledgement is returned to the context manager either authorizing or denying the request contained in the message.

The user mapping agent provides a similar service with respect to User IDs. A request is sent by the context manager for the login identifiers corresponding to a particular User ID, and a list of data is returned to the context manager. The context manager can then add the login identifiers corresponding to the User ID to the context data, in this case for the User subject, where it can be accessed by any application that has joined in the current context and that also has access to the User subject, which is secure.

Similarly, if the context administrator sends to the context server an LDAP message requesting a change to the passcode list or the map of User ID information, a security check is first performed, and then the transaction is either approved or disapproved.

The context server could be used to provide other services, as well. For example, the context server could provide a registry service, in which each context manager is registered. The registry would automate the inventorying process to a greater extent, allowing context managers and context servers to perform a handshake when a new module comes on line on a network, and the context manager to be automatically registered. The context administrator could also provide a default configuration service. Each registered context manager could be configured to the default configuration at the time it is registered, unless the default configuration is overridden.

The context server can be implemented as a server appliance. A server appliance is a network-connected server that services multiple client computers. Like conventional servers, a server appliance receives requests from client computers to perform specific tasks. The server performs a task requested and returns back to the client the result of performing the task. Unlike conventional servers that provide general purpose platforms for a wide range of computing tasks, a server appliance is singular in purpose. A server appliance contains specialized software and possibly specialized hardware to enable it to achieve its purpose. Thus, a server appliance can be optimized for the specific tasks that it is intended to perform, thereby reducing the cost and complexity of the server appliance when compared with the cost and complexity of a general purpose server configured for the same purpose.

The context administrator inventories the network by pinging all possible context manager addresses on a port registered with the IANA, according to one embodiment of the invention. The context administrator can be implemented on a Windows™ 98/2000/NT machine, and use the Windows™ Networking ping function to perform the required scan. Other operating systems such as Unix, Linux and the like, with their corresponding networking facilities can also be used.

According to some embodiments of the invention, communication between the context administrator and the context manager can occur using HTTP. However, context managers communicate with applications using the COM protocol, as mentioned above.

Therefore, in these embodiments of the invention, rather than add to the complexity and size of the context manager, a software daemon translates between HTTP and COM protocols. The context administrator sends signed messages to the context manager in HTTP, which are translated by the daemon into signed COM messages. The context manager returns XML messages, which the daemon wraps in HTTP to forward to the context administrator. Naturally, other communications protocols can be used, and even the native protocol used by the context manager can be used directly, in variations on embodiments of the invention.

It should be noted that for security reasons, the daemon is restricted to calling only COM objects which are part of the context manager module. Theoretically, an HTTP request could be for any COM object, but that would create a security breach by allowing the daemon to be used to gain access to other system components.

In order to effect proper communication between the context managers and the context servers, one configuration parameter set in the context managers is which context server, of a possible plurality on a given network, should be used. A failover mechanism can also be provided which would cause a secondary context server to be used in the event a primary context server failed to respond to a message.

Based upon the foregoing architecture, a new subject is implemented by the context administrator as follows. First the subject is defined in the context administrator by giving it a name and defining its schema. The definition is stored in the repository. Next, a user gestures to send out the configuration, causing an HTTP call to the context manager, through the daemon, to be sent out. Alternatively, the configuration can be stored in a context server in a configuration service, as discussed above. Finally, the context manger obtains and stores the new configuration information locally in a text file. This discussion, of course, assumes that one or more applications controlled by the context manager have a priori knowledge of the new subject, thus giving life and meaning to the new subject definition. If the subject has been defined to be secure, then the application will need a passcode to use the subject. Also, any new subject definition must have at least one application capable of setting data in the subject.

In one variation of the invention, the context manager can be embodied in a server appliance, as described above in connection with the context server. In such an embodiment of the invention, the applications may reside in a different computer, workstation, PC, etc. than the context manager appliance, which also may reside in a different computer, workstation, PC, etc. than the context administrator. The components of such a system which reside in different computers, workstations, PCs, etc. would be connected to each other through a network, such as a LAN, a WAN, an intranet, the Internet, etc.

In other variations of the invention, the structures and methods described herein can be combined with: the context sensitive web casting methods and apparatus disclosed in U.S. patent application Ser. No. 60/135,907, filed May 25, 1999, incorporated herein in its entirety by reference; the context management server appliance methods and apparatus disclosed in U.S. patent application Ser. No. 60/136,670, filed May 28, 1999, incorporated herein in its entirety by reference; the healthcare server appliances methods and apparatus disclosed in U.S. patent application Ser. No. 60/139,235, filed Jun. 14, 1999, incorporated herein in its entirety by reference; the HTTP Post message encoding of COM dispatch interface calls disclosed in U.S. patent application Ser. No. 60/139,145, filed Jun. 14, 1999, incorporated herein in its entirety by reference; the application context management methods and apparatus disclosed in U.S. patent application Ser. No. 60/146,722, filed Aug. 2, 1999, incorporated herein in its entirety by reference; and the context management web site methods and apparatus disclosed in U.S. patent application Ser. No. 60/145,681, filed Jul. 26, 1999, incorporated herein in its entirety by reference. This discussion and that contained in the referenced patent applications clearly suggest to the skilled artisan how such combinations would be made.

The invention has now been described and illustrated in connection with one embodiment and some variations thereof. Numerous other variations and modifications which will now be obvious to the skilled artisan are also contemplated as within the scope and spirit of the invention. The scope of the invention is not to be limited by the description of embodiments thereof, but only by the scope of the properly construed claims which follow.

What is claimed is:

1. At least one computer readable medium encoded with a program that, when executed, performs a method of administering a context management system that manages a context, the method comprising:

configuring a subject data definition which defines a plurality of subjects in the context using, for each subject, subject data that comprises a data item usable by a plurality of applications comprising at least a first application and a second application, the data item having a set of values comprising at least a first value corresponding to the first application and a second value corresponding to the second application, the set of values identifying the subject in the context, the value of the data item corresponding to the first application being exchangeable with the value of the data item corresponding to the second application when a user switches from the first application to the second application to retain the context, the plurality of subjects comprising a patient subject, a user subject and an encounter subject, and the subject data definition being defined in accordance with a Clinical Context Object Workgroup (CCOW) standard.

2. The at least one computer readable medium of claim 1, wherein the method further comprises:
identifying one or more available context managers to administer.

3. The at least one computer readable medium of claim 2, wherein identifying further comprises:
pinging possible context manager addresses to find the available context managers.

4. The at least one computer readable medium of claim 1, wherein the method further comprises:
maintaining in the subject data definition, information identifying which applications are allowed to access the subject.

5. The at least one computer readable medium of claim 4, wherein the method further comprises:
storing with each application a value which is a function of but not equal to a passcode for the application.

6. The at least one computer readable medium of claim 5, wherein the method further comprises:
encrypting the passcode to form the value.

7. The at least one computer readable medium of claim 1, wherein the method further comprises:
maintaining an inventory of applications whose context is managed.

8. The at least one computer readable medium of claim 7, wherein the method further comprises:
maintaining a map relating User IDs to login identifiers formatted for each application in the inventory.

9. The at least one computer readable medium of claim 2, wherein the method further comprises:
configuring communication parameters for the available context managers.

10. The at least one computer readable medium of claim 2, wherein the method further comprises:
generating a status report for the system.

11. The at least one computer readable medium of claim 2, wherein the method further comprises:
intervening in a context management process.

12. The at least one computer readable medium of claim 11, wherein intervening further comprises:
forcing an application out of a context.

13. The at least one computer readable medium of claim 11, wherein intervening further comprises:
canceling a transaction in progress.

14. The at least one computer readable medium of claim 11, wherein intervening further comprises:
shutting down a context manager.

15. The at least one computer readable medium of claim 1, wherein the method further comprises:
communicating with a context manager using a hypertext transport protocol.

16. The at least one computer readable medium of claim 15, wherein the hypertext transport protocol is HTTP 1.1.

17. An apparatus comprising:
at least one processor programmed to manage and administer a context, the at least one processor programmed to implement:
a context manager; and
an administration suite for configuring a subject data definition, the subject data definition defining a plurality of subjects in the context using, for each subject, subject data that comprises a data item usable by at least a first application and a second application, the data item having a set of values comprising at least a first value corresponding to the first application and a second value corresponding to the second application, the set of values identifying the subject in the context, the value of the data item corresponding to the first application being exchangeable with the value of the data item corresponding to the second application when a user switches from the first application to the second application to retain the context, the plurality of subjects comprising a patient subject, a user subject and an encounter subject, and the subject data definition being defined in accordance with a Clinical Context Object Workgroup (CCOW) standard.

18. The apparatus of claim 17, wherein the at least one processor is programmed so that the administration suite further comprises a context administrator and a context server.

19. The apparatus of claim 18, wherein the at least one processor is programmed so that the context server implements:
a passcode service;
a user mapping agent (UMA) service; and
a lightweight directory access protocol (LDAP) service.

20. The apparatus of claim 19, wherein the at least one processor is programmed so that the LDAP service further comprises:
a data storage module in which the passcode service stores encrypted passcodes and in which the user mapping agent service stores user-mapping data.

21. The apparatus of claim 18, wherein the at least one processor is programmed so that the context server further comprises:
a registry in which the context manager is registered.

22. The apparatus of claim 18, further comprising at least one storage device, and wherein the at least one processor is programmed so that the context server further comprises:
a configuration memory, in the at least one storage device, holding a common configuration used as a default configuration for the context manager.

23. The apparatus of claim 17, wherein the at least one processor comprises a single processor programmed to implement the context manager and the administration suite.

24. The apparatus of claim 17, wherein the at least one processor comprises at least a first processor programmed to implement the context manager and at least a second processor programmed to implement the administration suite.

25. The apparatus of claim 17, wherein the at least one processor is programmed so that the administration suite generates a log which includes information received from the context manager.

26. The apparatus of claim 17, wherein the log comprises an indication of a processing exception observed by the context manager.

27. The apparatus of claim 17, wherein the at least one processor is programmed so that the administration suite, subsequent to configuring the subject data definition, reconfigures the subject data definition, and communicates the reconfiguration of the subject data definition to the context manager.

28. The apparatus of claim 17, wherein the at least one processor is programmed so that the administration suite generates an inventory which includes the context manager.

29. The at least one computer readable medium of claim 2, wherein the method further comprises:
generating a log which includes information received from at least one of the available context managers.

30. The at least one computer readable medium of claim 29, wherein the act of generating the log comprises generating a log which includes an indication of a processing exception observed by the at least one of the available context managers.

31. The at least one computer readable medium of claim 2, wherein the method further comprises:
subsequent to the act of configuring the subject data definition, reconfiguring the subject data definition, and communicating the reconfiguration of the subject data definition to at least one of the available context managers.

32. The at least one computer readable medium of claim 2, wherein the method further comprises:
generating an inventory of the available context managers to administer.

* * * * *